United States Patent [19]

Wolvek

[11] Patent Number: 5,873,854
[45] Date of Patent: Feb. 23, 1999

[54] METHOD FOR PERCUTANEOUS INSERTION OF CATHETERS

[75] Inventor: Sidney Wolvek, Brooklyn, N.Y.

[73] Assignee: Datascope Investment Corp., Montvale, N.J.

[21] Appl. No.: 780,005

[22] Filed: Dec. 23, 1996

[51] Int. Cl.[6] .................................................. A61M 29/00
[52] U.S. Cl. ........................ 604/104; 604/105; 604/164; 604/178
[58] Field of Search ..................... 604/104, 105, 604/160, 161, 164, 165, 167, 158, 192, 198

[56] References Cited

U.S. PATENT DOCUMENTS

| Re. 34,993 | 7/1995 | Cicciu et al. | 600/18 |
|---|---|---|---|
| 4,166,469 | 9/1979 | Littleford | 128/784 |
| 4,243,050 | 1/1981 | Littleford | 128/784 |
| 4,345,606 | 8/1982 | Littleford | 128/784 |
| 4,897,077 | 1/1990 | Cicciu et al. | 600/18 |
| 5,167,634 | 12/1992 | Corrigan, Jr. et al. | 604/160 |
| 5,242,410 | 9/1993 | Melker | 604/164 |
| 5,250,033 | 10/1993 | Evans et al. | 604/160 |
| 5,391,183 | 2/1995 | Janzen et al. | 606/213 |
| 5,454,790 | 10/1995 | Dubrul | 604/164 |
| 5,489,273 | 2/1996 | Whitney et al. | 604/160 |

*Primary Examiner*—Danton D. DeMille
*Attorney, Agent, or Firm*—Fitzpatrick, Cella, Harper & Scinto

[57] ABSTRACT

A device for facilitating the insertion of balloon catheters and other devices into blood vessels, for example, the femoral artery, while presenting the minimal amount of obstruction to the flow of fluid through the vessel. The device is comprised of an introducer sheath having a hub and a short elongated section wherein when the hub abuts the patient's skin and the short elongated section is not long enough to reach the vessel. Also disclosed is a method for inserting a balloon catheter using the short introducer sheath.

6 Claims, 3 Drawing Sheets

METHOD FOR PERCUTANEOUS INSERTION OF CATHETERS

BACKGROUND OF THE INVENTION

1. Field of the Invention

The present invention relates generally to medical devices and to procedures that use catheters or similar devices. More particularly, the present invention relates to a short sheath designed primarily to facilitate the percutaneous insertion of a catheter and the method of percutaneously inserting such devices using said short sheath. The invention has particular utility when employed to facilitate the percutaneous insertion of balloon catheters, especially intra-aortic balloon catheters (IABs). However, the present invention also may be found to have utility in other medical procedures or applications.

2. Description of the Prior Art

Sheaths for use during medical procedures are well known, particularly for use during percutaneous procedures. As has been well known for many years, catheters, guide wires, or the like, may be introduced into a body channel, such as a vein or artery, through a guide sheath or without a sheath. For convenience, unless the context indicates otherwise, the term "artery" will be used herein in a generic sense to encompass both veins and arteries as well as other body cavities.

Generally, before inserting a catheter into a patient's artery or vein, a hollow needle is inserted through the skin and the subcutaneous tissue until it enters the vein or artery. Especially when an artery like the femoral artery is entered, spurting of blood from the hub at the proximal end of the needle indicates that the needle tip (its distal end) is in the artery. A guide wire is then passed through the needle into the lumen of the artery, whereupon the needle is removed and discarded. A dilator, often with a guide sheath or introducer sheath attached, can then be passed over the guide wire into the artery. A dilator, or a series of progressively larger dilators, are used to enlarge the channel or passageway into the artery so as to facilitate passage of the sheath. Having served its purpose, the dilator is then removed and discarded, leaving the introducer sheath in the artery. The sheath is then pushed further into the artery until sufficiently inserted to serve the purpose. At that point, its distal end is well into the artery, with most of the body of the sheath resident in the blood stream. A catheter can then be inserted into the artery by sliding it through the introducer sheath.

As indicated above, sheaths are well known in the art. For example, one such sheath is disclosed in U.S. Pat. No. 5,167,634 (Corrigan et al.) owned by the assignee of the instant invention. As can be seen, the sheath of the Corrigan reference has, near its proximal end, two wings. Among other functions, those wings limit the insertion of the sheath into the artery. The sheath of the Corrigan reference is a peelable sheath that can be split longitudinally so as to permit removal after it has served its purpose. Perhaps more common are non-peelable sheaths that remain resident in the artery during the entire procedure.

While catheters are frequently inserted through sheaths, it has long been known that they can also be inserted in a sheathless fashion. Each method has its advantages and each has its drawbacks. Use of a sheath provides guidance and a smooth path for the catheter through the skin, the subcutaneous tissue and through a portion of the artery. The sheath, however, when it is resident in the artery is an added obstruction to the flow of blood to the lower extremities and, especially in severely sclerotic or small patients, this obstruction can be of critical importance.

In sheathless insertions, since there is no sheath, there is nothing, except for the catheter itself, to obstruct the blood flow. However, some physicians are reluctant to perform sheathless insertions particularly of relatively large balloon catheters like IABs, because of the resistance often encountered in passing the uncovered balloon through the skin and subcutaneous tissue. The force necessary to overcome that resistance may result in kinking of the guide wire and/or the balloon. The feel of the balloon as it passes through this region is sometimes felt to be a sign of trouble or excessive trauma.

SUMMARY OF THE INVENTION

The present invention is designed to capitalize on the advantages of both methods while avoiding their disadvantages. It accomplishes this by employing an introducer sheath which is very much shorter than traditional sheaths. A sheath according to this invention is one which will guide the catheter through the skin and subcutaneous tissue but preferably will not enter the artery. The sheath of the instant invention is comprised of a short longitudinal sheath body section, preferably shorter than about 5 cm., with a radially extending section at its proximal end.

In accordance with this invention, an insertion technique is provided which enables a physician to insert a catheter percutaneously without encountering difficulties in getting through the skin and subcutaneous tissue and without placing a sheath in the artery that will interfere with the flow of blood.

BRIEF DESCRIPTION OF THE DRAWINGS

A more complete appreciation of the present invention and the many attendant features and advantages thereof will become more apparent by reference to the following detailed description of a preferred embodiment thereof together with the accompanying drawings wherein.

DETAILED DESCRIPTION OF A PREFERRED EMBODIMENT

Figure 1:
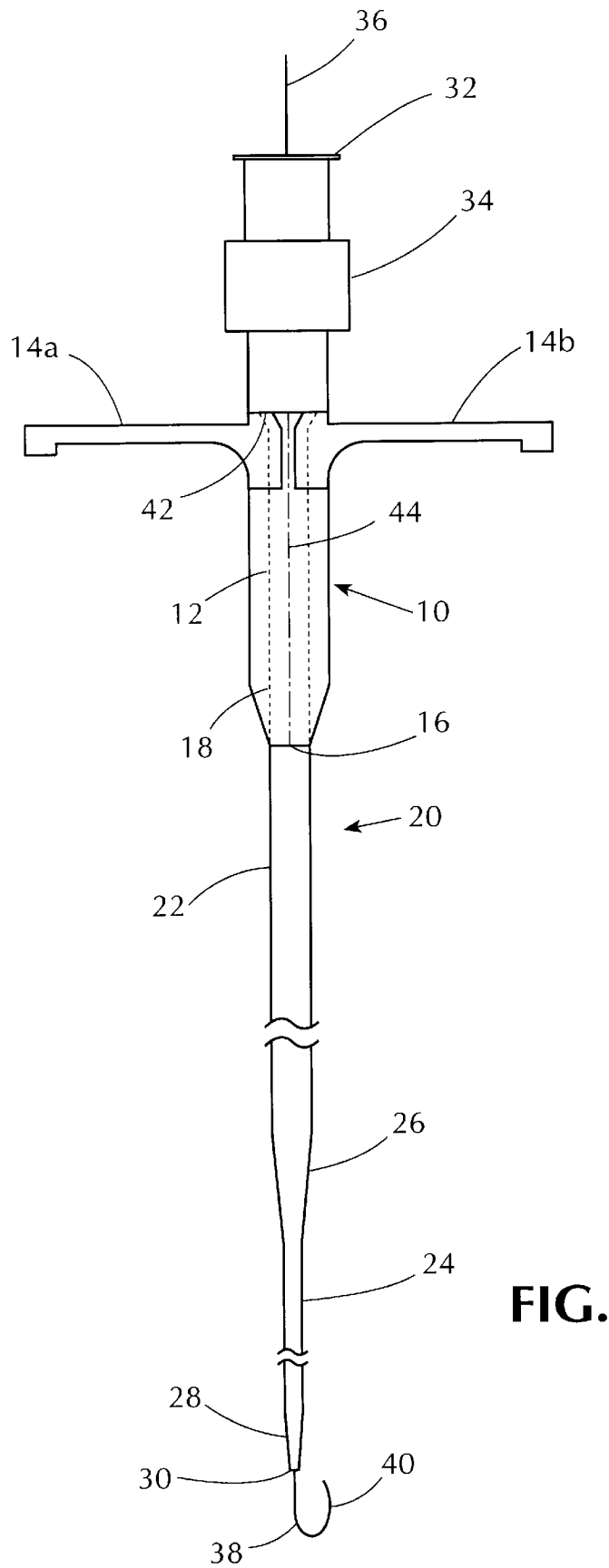
FIG. 1 is a plan view of a system according to the instant invention for percutaneous insertion of an IAB.
Figure 2:
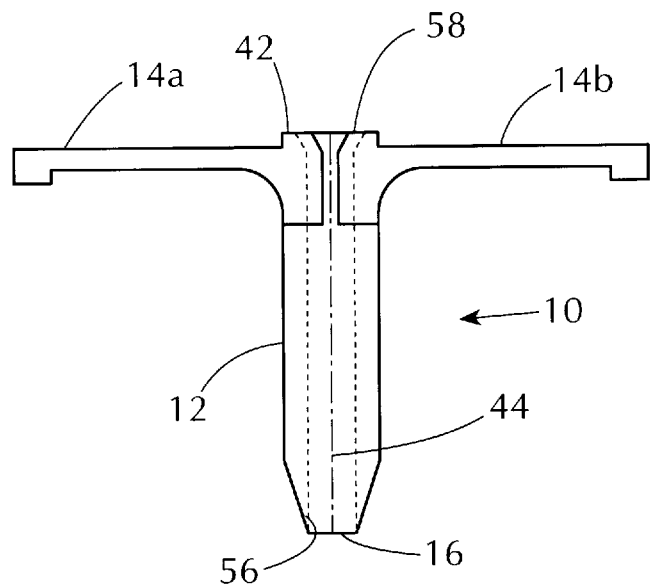
FIG. 2 is a plan view of a short sheath according to the present invention.
Figure 3:
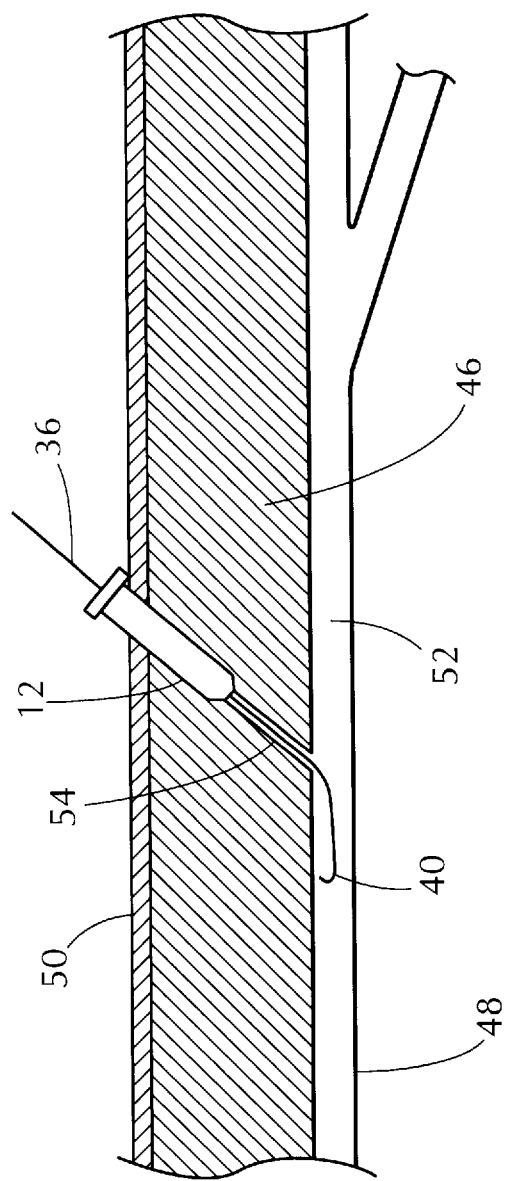
FIG. 3 is schematic view of a short sheath, according to the invention, inserted in a patient in preparation for receiving an IAB.

Referring to the drawings where like reference numerals identify like or similar parts throughout, FIGS. 1–3 illustrate one embodiment of the present invention. The peelable short sheath 10 illustrated in the drawings generally comprises a sheath body 12 and a pair of wings 14a and 14b.

Sheath body 12 generally comprises a flexible plastic tube having a hollow cylindrical cross-section defining a through lumen from its distal end 16 to its proximal end 42. The distal end 16 of sheath body 12 has an inward taper 18 to facilitate the transition from the dilator 20 to the sheath. The size of the sheath lumen 56 is large enough to accommodate the main body section 22 of dilator 20. At its proximal end, lumen 56 is provided with an inside taper or chamfer 58 to form a funnel-like entrance to lumen 56 so as to facilitate entry of a catheter or other device into said lumen.

Dilator 20 is comprised of a main body section 22, a narrow body section 24 and a tapered section 26 between the main body and narrow body sections. The dilator 20 also has a second taper 28 at its distal end 30. At its proximal end 32, the dilator has a hub 34 and through the entire dilator, from its distal end 30 to its proximal end 32, there is a lumen of a size sufficient to accommodate guide wire 36. Guide wire 36 is provided, at its distal end 38 with a flexible J-tip 40.

Sheath body 12 is also provided with a score or separation line 44 running longitudinally the entire length of sheath 10 from its distal end 16 to its proximal end 42. A similar separation line (not shown) is provided on the opposite side of sheath body 12. Each of wings 14a and 14b is connected to one side of sheath body 12. When wings 14a and 14b are pulled outwardly away from each other, they cause sheath body 12 to separate along its two opposing separation lines.

As noted earlier, sheath body 12 is substantially shorter than traditional sheath bodies. Sheath body 12 is preferably between about 5 cm. and about 1 cm. long, most preferably between 1.5 cm. and 3.5 cm. The actual length of the sheath used in any given procedure may vary from patient to patient. A physician may wish to use a relatively long sheath (about 5 cm. or longer) for a large patient with a thick layer of fat or muscle between the skin and the artery whereas with a thin patient or a young child a smaller sheath (about 1 cm. or even shorter) might be more appropriate.

A physician using the sheath of the instant invention would first select the proper length sheath, preferably one that would line most of the channel or passageway 54 through the subcutaneous tissue 46 but would not enter the artery 48. The physician or other health professional would then prepare the sheath dilator set by sliding dilator 20 through the lumen in sheath body 12 until hub 34 reaches proximal end 42 of sheath 10. The sheath dilator set would then be set aside.

The physician would then palpate the insertion region until the underlying artery 48 is located. A needle (not shown) would then be inserted through the skin 50 and the subcutaneous tissue 46 until the tip of the needle is in the lumen 52 of the artery, as evidenced by the spurting of blood from the needle. Guide wire 36 would then be inserted through the needle into the artery and the needle would then be removed from over the guide wire and discarded. Then, prior to inserting the dilator, a scalpel (not shown) would be used to make a small nick in the skin and the immediately underlying tissue so as to facilitate penetration of the dilator. The sheath dilator set would then be threaded over the proximal end of guide wire 36 and passed along the wire until distal end 30 reaches skin 50. The physician would then push the dilator down through the skin and the subcutaneous tissue and into the arterial lumen 52 thereby enlarging wound channel 54. Continued feeding of dilator 20 along guide wire 36 would cause further enlargement of the passageway by forcing taper 26 and then main body 22 through wound channel 54.

The sheath dilator set would be pushed along guide wire 36 until wings 14b and 14a reach skin 50. At that point dilator 20 would be removed, leaving only sheath body 12 and guide wire 36 in wound channel 54 with the distal end 16 of sheath 10 in channel 54 but not in lumen 52 of artery 48. The physician would then insert the catheter or other device over guide wire 38 and through the lumen of sheath 10 into the artery and advance it as needed until it reaches its desired location. If the catheter being inserting is an intra-aortic balloon catheter, it would be advanced until the balloon chamber is resident in the descending thoracic aorta. With the catheter or other device properly located in the body, the physician would have the option of leaving sheath 10 in place or using wings 14a and 14b to split the sheath in two and removing it entirely from the wound and from the balloon catheter.

Figure 4:
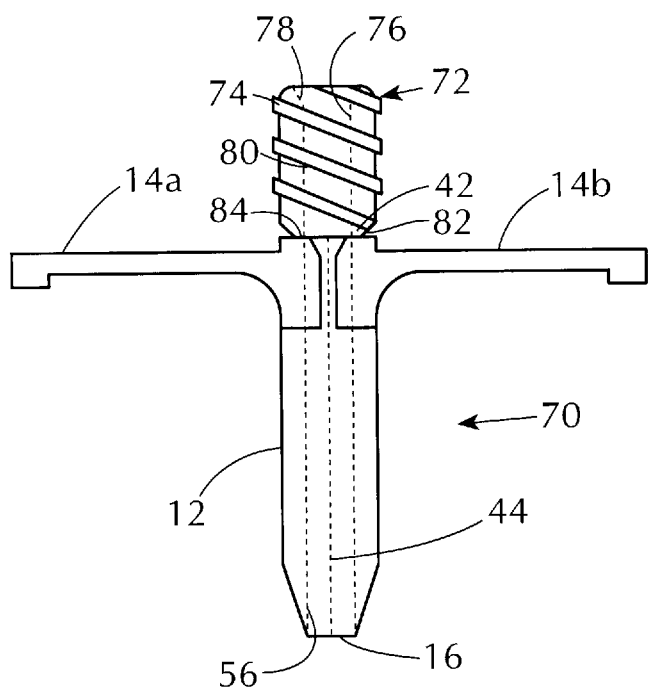
FIG. 4 is a plan view of a second embodiment of a short sheath according to the present invention.

FIG. 4 depicts a second embodiment of a short sheath according to the present invention. Sheath 70 of FIG. 4 incorporates all of the features of sheath 10 of the previous Figs. but, in addition, sheath 70 includes a hub 72 having threads 80 on the external periphery thereof. Hub 72 permits fluid-tight attachment to sheath 70 of various accessories, for example a sealing sheath.

Hub 72 has a through lumen 76 that meets lumen 56 at proximal end 42 and both lumens are of substantially the same cross-sectional configuration. Lumen of hub 72 is provided with an inside taper or chamfer 78 to form a funnel-like entrance to lumen 76.

The embodiment of FIG. 4 can be used in precisely the same way as the embodiment of FIG. 1. Alternatively, the FIG. 4 embodiment can be inserted with a sealing sheath (not shown) or other accessary attached to hub 72. A sealing sheath could be used, for example, to reduce potential contamination of the region of the balloon catheter adjacent the wound.

If the physician decides to use the sheath of FIG. 4 without any accessories attached to hub 72, the score line on the hub permits it to be split, at the same time as sheath 10 in split, by use of wings 14(*a*) and 14(*b*). The sheath together with the hub can then be removed entirely from the wound and from the balloon catheter.

Alternatively, in the embodiment of FIG. 4, hub 72 could be provided with reduced diameter section 82, forming a circumfercial separation line 84 at its base to permit separating the hub from the remainder of the sheath.

Although the sheath of the preferred embodiment has been described as having a pair of radially opposed wings at its proximal end, other radial extending configurations can be used as well. Similarly, although in the preferred embodiment the sheath has been described as a splitable sheath having opposed separation lines, the scope of this invention is intended to cover non-splitable sheaths also.

As those skilled in the art will understand, while the subject invention has been described in the context of inserting a catheter or similar device into an artery, in its broader scope, the invention is not so limited. Rather, it can be used to facilitate insertion of catheters or other similar devices into other body cavities.

Sheaths according to the subject invention are preferably made of polytetrafluoroethylene (TEFLON) or polypropylene, or any other biocompatible material. Indeed, because in its preferred configuration the sheath is very short, flexibility is not an absolute requirement, although it is believed that a flexible sheath would be preferred.

Numerous other embodiments, variations and modifications will be readily apparent to those skilled in the art and it is intended that all such embodiments, variations and modifications fall within the scope of the invention herein described and claimed and are intended to be covered thereby. It should be noted that the above description of one embodiment is illustrative only and is not intended to limit the scope of the present invention, which is defined by the following claims.

What is claimed is:

1. A method for inserting an intra-aortic balloon catheter through a patient's skin and subcutaneous tissue and into the femoral artery comprising the steps of:

(a) puncturing the patient's skin, subcutaneous tissue and femoral artery to create a channel from outside the patient's body into the femoral artery, (b) inserting a guide wire through said channel into said artery, (c) dilating said channel to enlarge its diameter to a size sufficient to permit passage therethrough of said catheter, (d) inserting a sheath into said enlarged channel without permitting said sheath to enter said artery, and (e) inserting said catheter over said guide wire and through said sheath into said artery.

2. The method according to claim 1 wherein said dilating step is accomplished through the insertion into said channel of a dilator over said guide wire and wherein said sheath is inserted into said channel over said dilator, further including the step of removing said dilator before inserting said catheter.

3. The method according to claim 1 wherein said sheath is a splitable sheath and further including the step of splitting said sheath and removing same after said catheter has entered said artery.

4. The method according to claim 1 wherein said sheath has a distal end and a proximal end and wherein it has a radially extending portion at said proximal end and wherein when said sheath is inserted into said channel it is inserted until said radially extending portion abuts said skin of said patient.

5. The method according to claim 1 wherein said sheath has a distal end and a proximal end and wherein it has a radially extending portion at said proximal end and wherein the axial length of said sheath from said radially extending portion to said distal end is less than the length of said channel from said patient's skin to said artery.

6. The method according to claim 1 wherein said sheath has attached adjacent its proximal end a hub for attachment thereto of accessories, said method further comprising separating said hub from said sheath after the insertion of said sheath into said channel.

* * * * *